(12) United States Patent
Baril et al.

(10) Patent No.: US 11,253,240 B2
(45) Date of Patent: Feb. 22, 2022

(54) TISSUE SPECIMEN RETRIEVAL DEVICES

(71) Applicant: COVIDIEN LP, Mansfield, MA (US)

(72) Inventors: Jacob C. Baril, Norwalk, CT (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 227 days.

(21) Appl. No.: 16/566,481

(22) Filed: Sep. 10, 2019

(65) Prior Publication Data

US 2021/0068798 A1 Mar. 11, 2021

(51) Int. Cl.
*A61B 17/00* (2006.01)

(52) U.S. Cl.
CPC ........... *A61B 17/00234* (2013.01); *A61B 2017/00287* (2013.01); *A61B 2017/00867* (2013.01); *A61B 2017/00991* (2013.01)

(58) Field of Classification Search
CPC .... A61B 17/00234; A61B 2017/00287; A61B 2017/00867; A61B 2017/00991; A61B 2017/00367; A61B 2017/00407
See application file for complete search history.

(56) References Cited

U.S. PATENT DOCUMENTS

| | | | |
|---|---|---|---|
| 5,341,815 A * | 8/1994 | Cofone | A61B 17/00234 600/562 |
| 6,059,793 A | 5/2000 | Pagedas | |
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |
| 6,344,026 B1 | 2/2002 | Burbank et al. | |
| 6,350,266 B1 | 2/2002 | White et al. | |
| 6,350,267 B1 | 2/2002 | Stefanchik | |
| 6,358,198 B1 | 3/2002 | Levin et al. | |
| 6,368,328 B1 | 4/2002 | Chu et al. | |
| 6,383,195 B1 | 5/2002 | Richard | |
| 6,383,197 B1 | 5/2002 | Conlon et al. | |
| 6,387,102 B2 | 5/2002 | Pagedas | |

(Continued)

*Primary Examiner* — Brooke Nicole Labranche
(74) *Attorney, Agent, or Firm* — Carter, DeLuca & Farrell LLP

(57) ABSTRACT

A tissue specimen retrieval device includes a first shaft and a second shaft telescopically movable relative to the first shaft. The second shaft supports an end effector assembly. The end effector assembly includes a tissue specimen bag supported by a first arm and a second arm extending from the distal end portion of the second shaft. A brim defines a bag mouth. The first and second arms open the bag mouth. A bag body extends from the brim and defines a pouch for a tissue specimen. The bag body reversibly furls and unfurls about the brim. The first arm includes a first upper arm and a first lower arm defining a first channel. The second arm includes a second upper arm and a second lower arm defining a second channel. The bag body is supported in the first channel and the second channel when the bag body is furled.

17 Claims, 8 Drawing Sheets

(56) References Cited

U.S. PATENT DOCUMENTS

| | | |
|---|---|---|
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,654,283 B2 | 2/2010 | Seto et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinsk et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,542 B2 | 10/2016 | Hurley et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,624,638 B2 | 4/2017 | Lebreton et al. |
| 9,629,618 B2 | 4/2017 | Davis et al. |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2011/0184431 A1* | 7/2011 | Parihar ................ A61B 17/00 606/114 |
| 2019/0321018 A1* | 10/2019 | Prior ................ A61B 17/00234 |

\* cited by examiner

TISSUE SPECIMEN RETRIEVAL DEVICES

BACKGROUND

Technical Field

The present disclosure relates to tissue specimen retrieval from an internal body cavity and, more particularly, to tissue specimen retrieval devices to facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment.

SUMMARY

In accordance with an aspect of the present disclosure, a tissue specimen retrieval device includes a first shaft and a second shaft telescopically movable relative to the first shaft. The second shaft supports an end effector assembly at a distal end portion thereof. The second shaft is movable relative to the first shaft between a retracted position in which the end effector assembly is disposed within the first shaft, and a deployed position in which the end effector assembly extends distally from the first shaft. The end effector assembly includes a tissue specimen bag supported by a first arm and a second arm. The first and second arms extend from the distal end portion of the second shaft. A brim defines a bag mouth. The first and second arms open the bag mouth when the second shaft is in the deployed position. A bag body extends from the brim and defines a pouch for a tissue specimen. The bag body reversibly furls and unfurls about the brim. The first arm includes a first upper arm and a first lower arm defining a first channel therebetween. The second arm includes a second upper arm and a second lower arm defining a second channel therebetween. The bag body or a portion thereof is supported in the first channel and the second channel when the bag body is furled.

In some aspects, the bag body includes one or more spines operably associated with the brim and depending therefrom. The spine reversibly furls and unfurls the bag body about the brim. The brim may include a shape memory alloy including nickel and/or titanium. The spine may include a shape memory alloy including nickel and/or titanium.

In some aspects, the brim has a width of less than 15 mm. In other aspects, the furled bag body is supported between the first upper arm, the first lower arm, the second upper arm and the second lower arm in the first shaft when the second shaft is in the retracted position. The first upper arm, the first lower arm, the second upper arm and the second lower arm may each include a shape memory alloy including nickel and/or titanium.

In some aspects, the first arm is selectively detachable from the second arm.

In accordance with an aspect of the present disclosure, a method of deploying a tissue specimen bag includes telescopically advancing a second shaft from a first shaft. The second shaft supports a tissue specimen bag at a distal end portion thereof. The tissue specimen bag includes a first arm and a second arm. The first and second arms extend from the distal end portion of the second shaft. A brim defines a bag mouth. The first and second arms open the bag mouth. A bag body extends from the brim and defines a pouch for a tissue specimen. The bag body includes one or more spines operably associated with the brim and depending therefrom. The spine reversibly furls and unfurls the bag body about the brim. The first arm includes a first upper arm and a first lower arm defining a first channel therebetween. The second arm includes a second upper arm and a second lower arm defining a second channel therebetween. The bag body or a portion thereof is supported in the first channel and the second channel when the bag body is furled. The method includes opening the bag mouth by expanding the first and second arms. The bag body is unfurled from the first channel and the second channel by unwinding the spine to expand the pouch.

BRIEF DESCRIPTION OF THE DRAWINGS

The accompanying drawings, which are incorporated in and constitute a part of this specification, illustrate embodiments of the present disclosure and, together with the detailed description below, serve to further explain the present disclosure, in which.

DETAILED DESCRIPTION

Figure 1:
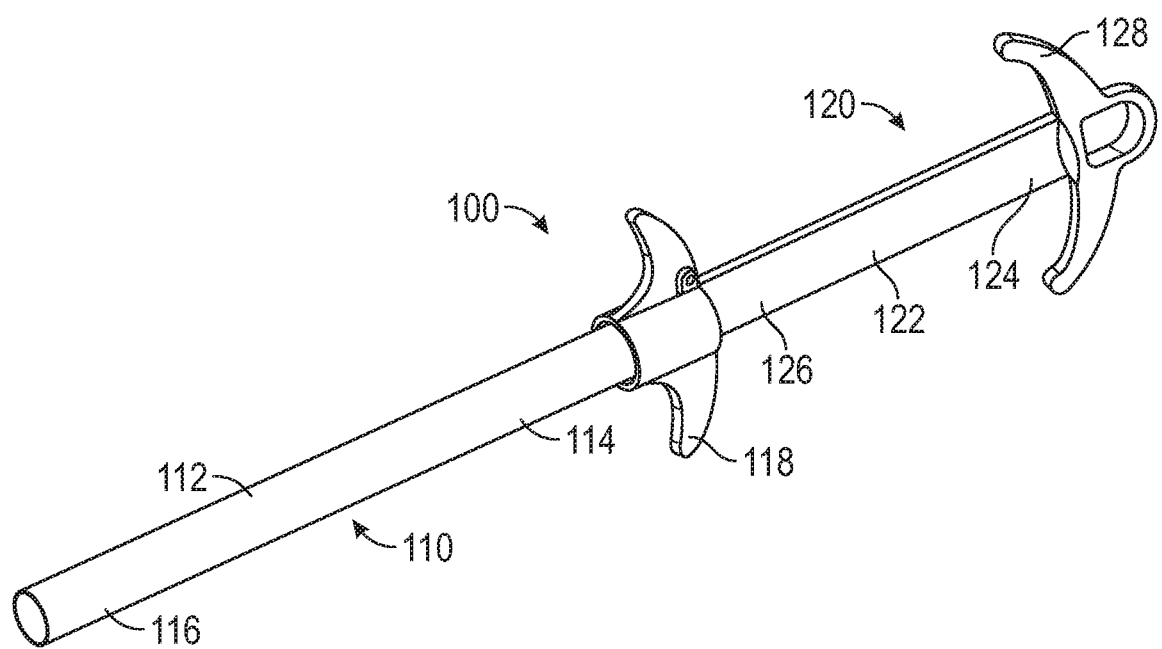
FIG. 1 is a perspective view of a tissue specimen retrieval device provided in accordance with aspects of the present disclosure, disposed in a retracted position.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

"About" or "approximately" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the present disclosure should typically be considered as available and applicable to other similar features or aspects in another exemplary embodiment of the present disclosure. Accordingly, technical features described herein according to one exemplary embodiment of the present disclosure may be applicable to other exemplary embodiments of the present disclosure, and thus duplicative descriptions may be omitted herein.

Exemplary embodiments of the present disclosure will be described more fully below (e.g., with reference to the accompanying drawings). Like reference numerals may refer to like elements throughout the specification and drawings.

Figure 2:
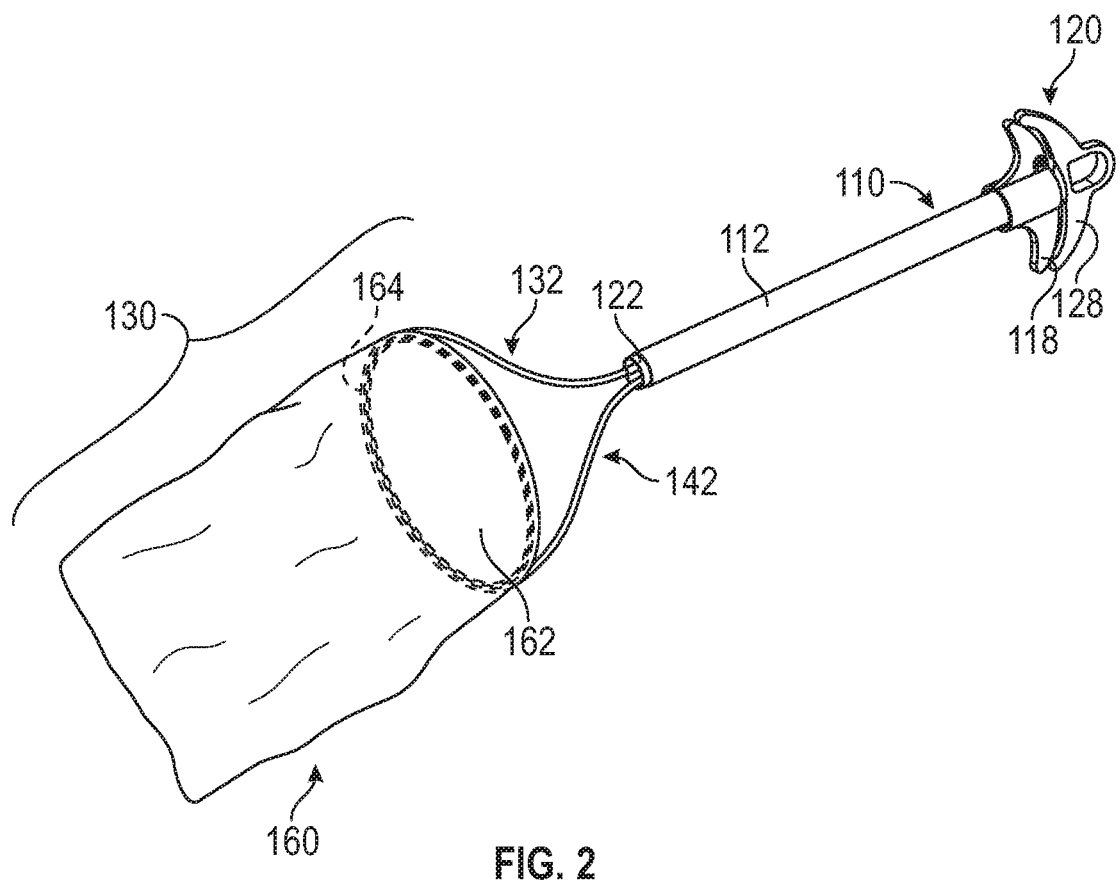
FIG. 2 is a perspective view of the tissue specimen retrieval device of FIG. 1, disposed in a deployed position.

Referring to FIGS. 1-2, a tissue specimen retrieval device provided in accordance with the present disclosure is shown generally identified by reference numeral 100. Tissue specimen retrieval device 100 includes a first body 110, a second body 120, and an end effector assembly 130 including a specimen bag 160. The phrases "specimen bag" and "specimen retrieval bag" may be used interchangeably herein. First body 110 includes a first shaft 112 defining a proximal end portion 114 and a distal end portion 116. First body 110 further includes a first handle 118 disposed at proximal end portion 114 of first shaft 112. First handle 118 may be engaged with proximal end portion 114 of first shaft 112, monolithically formed with proximal end portion 114 of first shaft 112, or otherwise secured thereto in any suitable manner that enables a user to grasp and manipulate first handle 118 to thereby control manipulation of first shaft 112.

Second body 120 includes a second shaft 122 defining a proximal end portion 124 and a distal end portion 126. Second shaft 122 supports end effector assembly 130 at distal end portion 126 of second shaft 122 and is telescopically slidably within and relative to first shaft 112 between a retracted position of tissue specimen retrieval device 100 (FIG. 1), wherein end effector assembly 130 is disposed within first shaft 112, and a deployed position of tissue specimen retrieval device 100 (FIG. 2), wherein end effector assembly 130 extends distally from first shaft 112. Second body 120 further includes a second handle 128 disposed at proximal end portion 124 of second shaft 122. Second handle 128 may be engaged with proximal end portion 124 of second shaft 122, monolithically formed with proximal end portion 124 of second shaft 122, or otherwise secured thereto in any suitable manner that enables a user to grasp and manipulate second handle 128 to thereby control manipulation of second shaft 122. Second handle 128, more specifically, is movable relative to first handle 118 from a spaced-apart position (FIG. 1) to an approximated position (FIG. 2) to move tissue specimen retrieval device 100 from the retracted position (FIG. 1), wherein end effector assembly 130 is disposed within first shaft 112, to the deployed position (FIG. 2), wherein end effector assembly 130 extends distally from first shaft 112.

Figure 3:
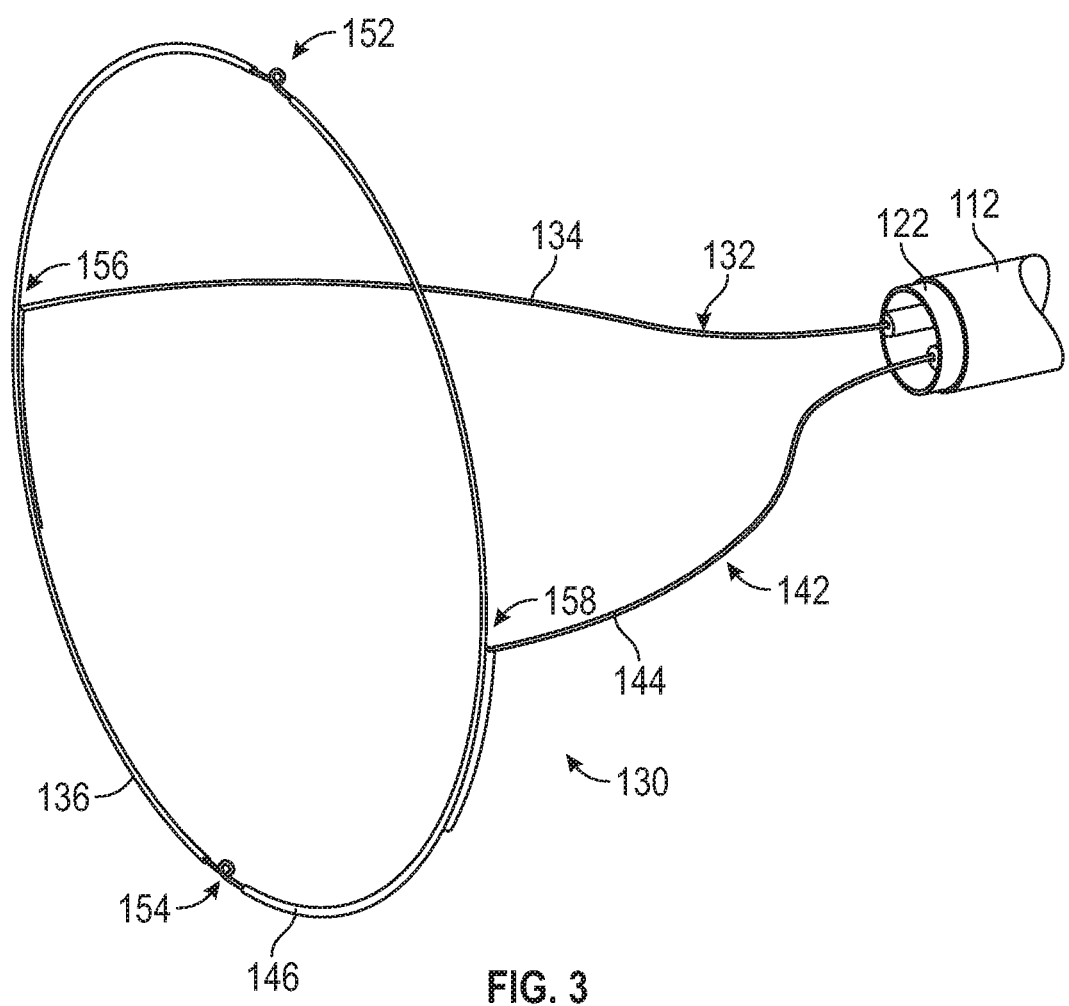
FIG. 3 is an enlarged, perspective view of the end effector assembly of the tissue specimen retrieval device of FIG. 1 with the specimen bag removed therefrom.

Referring to FIGS. 2 and 3, end effector assembly 130, as noted above, is supported at distal end portion 126 of second shaft 122. End effector assembly 130, more specifically, includes first and second arms 132, 142 extending distally from distal end portion 126 of second shaft 122 and a specimen bag 160 supported by and depending from first and second arms 132, 134. Each of first and second arms 132, 142 includes a proximal segment 134, 144 engaged with and extending distally from distal end portion 126 of second shaft 122, and a distal segment 136, 146 coupled to the respective proximal segment 134, 144 and extending distally therefrom.

Proximal segments 134, 144 of arms 132, 142, respectively, are substantially co-planar with one another so as to define a plane bisecting proximal segments 134 and 144, and are formed from resiliently flexible material, e.g., nitinol tubing, that biases proximal segments 134, 144 towards a first expanded position. Proximal segments 134, 144 each define, in the first expanded position, a curvature along at least a portion of the length thereof such that the proximal portions of proximal segments 134, 144 are relatively closer to one another and the distal portions of proximal segments 134, 144 are relatively father apart from one another.

Proximal segments 134, 144 of arms 132, 142, respectively, may be resiliently flexed from the first expanded position towards a first collapsed position, wherein the curvatures of proximal segments 134, 144 are at least partially eliminated and the distal portions of proximal segments 134, 144 are moved closer to one another, e.g., such that proximal segments 134, 144 are moved towards a substantially parallel orientation. Proximal segments 134, 144 are configured to resiliently flex within the plane defined thereby such that proximal segments 134, 144 remain substantially co-planar with one another in each of and during movement between the first expanded and first collapsed positions.

As an alternative or in addition to curved and/or resilient flexible configurations, proximal segments 134, 144 may define linear and/or substantially rigid configurations including one or more joints therealong to enable movement of proximal segments 134, 144 or portions thereof between the first expanded and first collapsed positions.

Distal segments 136, 146 of arms 132, 142, respectively, are substantially co-planar with one another so as to define a plane bisecting distal segments 136 and 146. Distal segments 136, 146 define curved configurations and are oriented relative to one another to cooperatively define a substantially oval-shaped configuration. Distal segments 136, 146 are formed from resiliently flexible material, e.g., nitinol tubing, that biases distal segments 136, 146 to a second expanded position, wherein distal segments 136, 146 cooperate to define a more-circular configuration.

Distal segments 136, 146 of arms 132, 142, respectively, are coupled to one another at first ends thereof via a first joint 152 and at second, opposite ends thereof via a second joint 154. In embodiments, first and second joints 152, 154 provide a bias that contributes to biasing distal segments 136, 146 towards the second expanded position; in other embodiments, the bias towards the second expanded position is provided by distal segments 136, 146 themselves without substantial bias imparted by first and second joints 152, 154. In either configuration, joints 152, 154 and distal segments 136, 146 are configured to move against the bias(es) such that distal segments 136, 146 are moved from the second expanded position, wherein distal segments 136, 146 cooperate to define the more-circular configuration, to a second collapsed position, wherein distal segments 136, 146 cooperate to define an elongated, oval-shaped configuration. Distal segments 136, 146 are configured to resiliently flex, and first and second joints 152, 154 are configured to move, within the plane defined by distal segments 136, 146, e.g., such that distal segments 136, 146 remain substantially co-planar with one another in each of and during movement between the second expanded and second collapsed positions. First and second joints 152, 154 may be hinge joints (living or multi-component hinges), pivot joints, torsion spring joints (similarly as detailed below), or other suitable joints.

As an alternative or in addition to distal segments 136, 146 cooperating to define an oval-shaped configuration and/or being resiliently flexible, distal segments 136, 146 may define linear and/or substantially rigid configurations including a plurality of joints, e.g., two to four joints, five joints, etc., defining a polygonal configuration, while still being movable between the second expanded position and the second collapsed position.

With reference to FIG. 2, distal segments 136, 146 support specimen bag 160 thereon with specimen bag 160 depending therefrom. Specimen bag 160 may be formed from any suitable bio-compatible material (or materials), e.g., ripstop nylon, configured to retain a tissue specimen therein. Specimen bag 160 defines at least one opening, e.g., open end 162 thereof, for receipt of a tissue specimen therein. Specimen bag 160 may include one or more channels 164 formed about at least a portion of the perimeter of open end 162 thereof for retaining distal segments 136, 146 of arms 132, 142, respectively, therein to support specimen bag 160 on distal segments 136, 146. Alternatively, open end 162 of specimen bag 160 may be welded, adhered, or otherwise affixed to or about distal segments 136, 146 to support specimen bag 160 thereon.

The one or more openings of specimen bag 160, e.g., open end 162, may include a cinch cord (not shown) disposed thereabout to enable selective closure of the opening. Specimen bag 160 may be disengaged from distal segments 136, 146 upon cinching closed open end 162 of specimen bag 160, retraction of end effector assembly 130 back towards the retracted position (FIG. 1), using a separate instrument, e.g., grasping device, and/or in any other suitable manner Turning again to FIGS. 2 and 3, distal segments 136, 146 of arms 132, 142 are coupled to respective proximal segments 134, 144 of arms 132, 142 via third and fourth joints 156, 158, respectively, to enable the collapsing of end effector assembly 130 wherein distal segments 136, 146 are collapsed onto to proximal segments 134, 144. Third and fourth joints 156, 158 may be hinge joints (living or multi-component hinges), pivot joints, torsion spring joints (similarly as detailed below), or other suitable joints. Third and fourth joints 156, 158, more specifically, enable collapsing of distal segments 136, 146 relative to proximal segments 134, 144 from a third expanded position (see FIG. 4A), wherein the planes defined by distal segments 136, 146 and proximal segments 134, 144 are disposed in a first orientation relative to one another, to a third collapsed position (see FIG. 4B), wherein the planes defined by distal segments are disposed in a second orientation relative to one another. Third and fourth joints 156, 158 are configured to bias distal segments 136, 146 towards the third expanded position relative to proximal segments 134, 144, wherein the planes defined thereby are disposed in the first orientation, although other configurations are also contemplated.

In embodiments, in the third expanded position, corresponding to the first orientation of the planes defined by distal segments 136, 146 and proximal segments 134, 144, the planes are disposed in substantially perpendicular orientation relative to one another; in other embodiments, the planes define an angle therebetween of from about 45 degrees to about 120 degrees; in still other embodiments, the planes define an angle therebetween of from about 60 degrees to about 105 degrees; and in yet other embodiments, the planes define an angle therebetween of from about 75 degrees to about 90 degrees.

In embodiments, in the third collapsed position, corresponding to the second orientation of the planes defined by distal segments 136, 146 and proximal segments 134, 144, the planes are disposed in substantially parallel orientation relative to one another; in other embodiments, the planes define an angle therebetween of from about 0 degrees to about 15 degrees; in still other embodiments, the planes define an angle therebetween of from about 0 degrees to about 10 degrees; and in yet other embodiments, the planes define an angle therebetween of from about 0 degrees to about 5 degrees.

Turning back to FIGS. 1 and 2, in the retracted position of tissue specimen retrieval device 100 (FIG. 1), as noted above, end effector assembly 130 is disposed within first shaft 112 of first body 110. In order to fit end effector assembly 130 within first shaft 112 in the retracted position of tissue specimen retrieval device 100 (FIG. 1), the end effector assembly 130 is collapsed from two orientations. Although described herein in terms of a first collapse followed by a second collapse, the present disclosure also contemplates that the first collapse follows the second collapses, or that at least portions of the first and second collapses are effected substantially simultaneously.

Figure 4A:
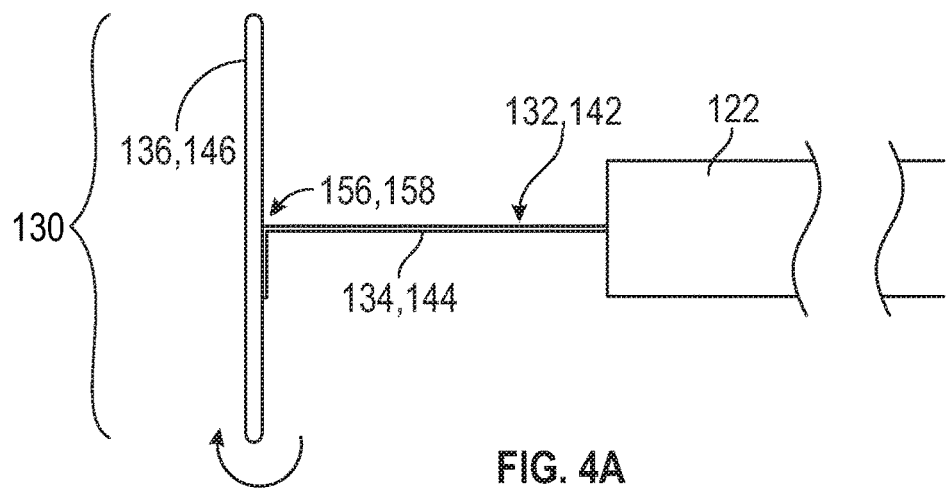
FIGS. 4A and 4B are side views of the end effector assembly of the tissue specimen retrieval device of FIG. 1 illustrating a first collapsing of the end effector assembly.
Figure 4B:
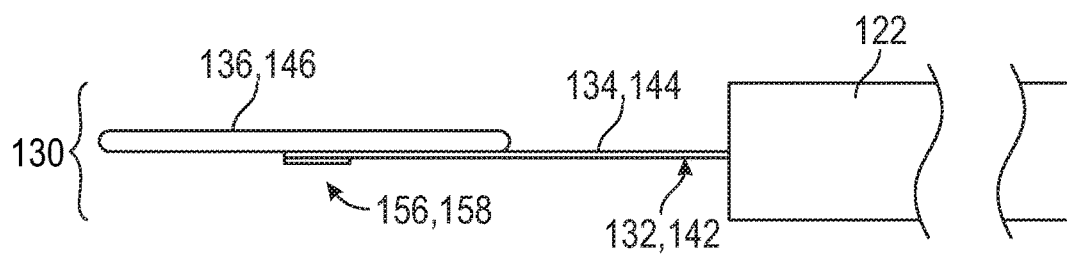

Referring to FIGS. 4A and 4B, the first collapse corresponds to the movement of distal segments 136, 146 of arms 132, 142 about third and fourth joints 156, 158, respectively, and relative to respective proximal segments 134, 144 from the third expanded position to the third collapsed position, as detailed above. This movement of distal segments 136, 146 about third and fourth joints 156, 158 to effect the first collapse occurs via relative movement of the planes defined by proximal segments 134, 144 and distal segments 136, 146, e.g., the plane defined by distal segments 136, 146 is moved relative to the plane defined by proximal segments 134, 144 during the first collapse.

Figure 5A:
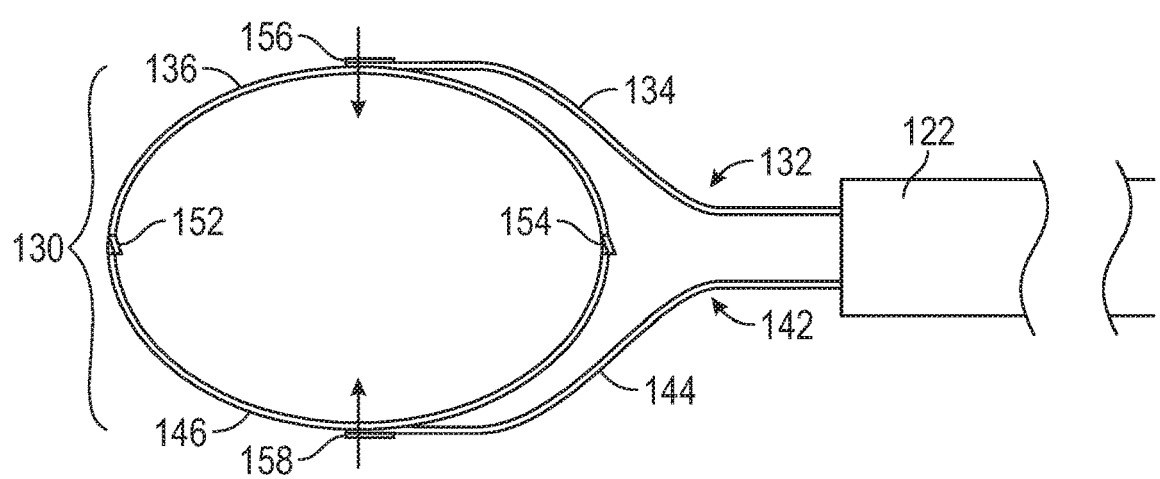
FIGS. 5A and 5B are top views of the end effector assembly of the tissue specimen retrieval device of FIG. 1 illustrating a second collapsing of the end effector assembly.
Figure 5B:
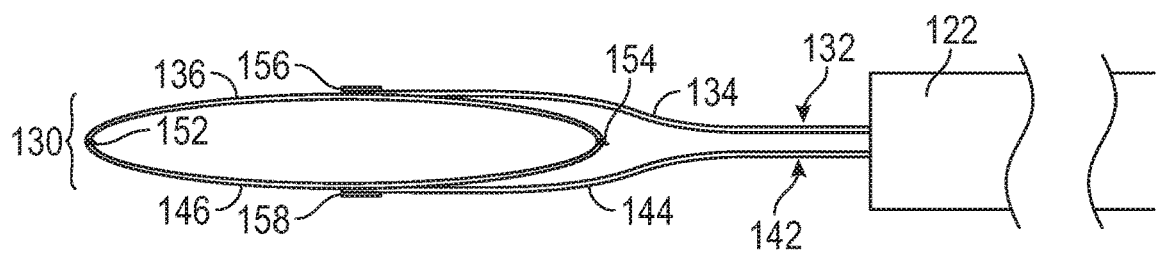
Figure 6:
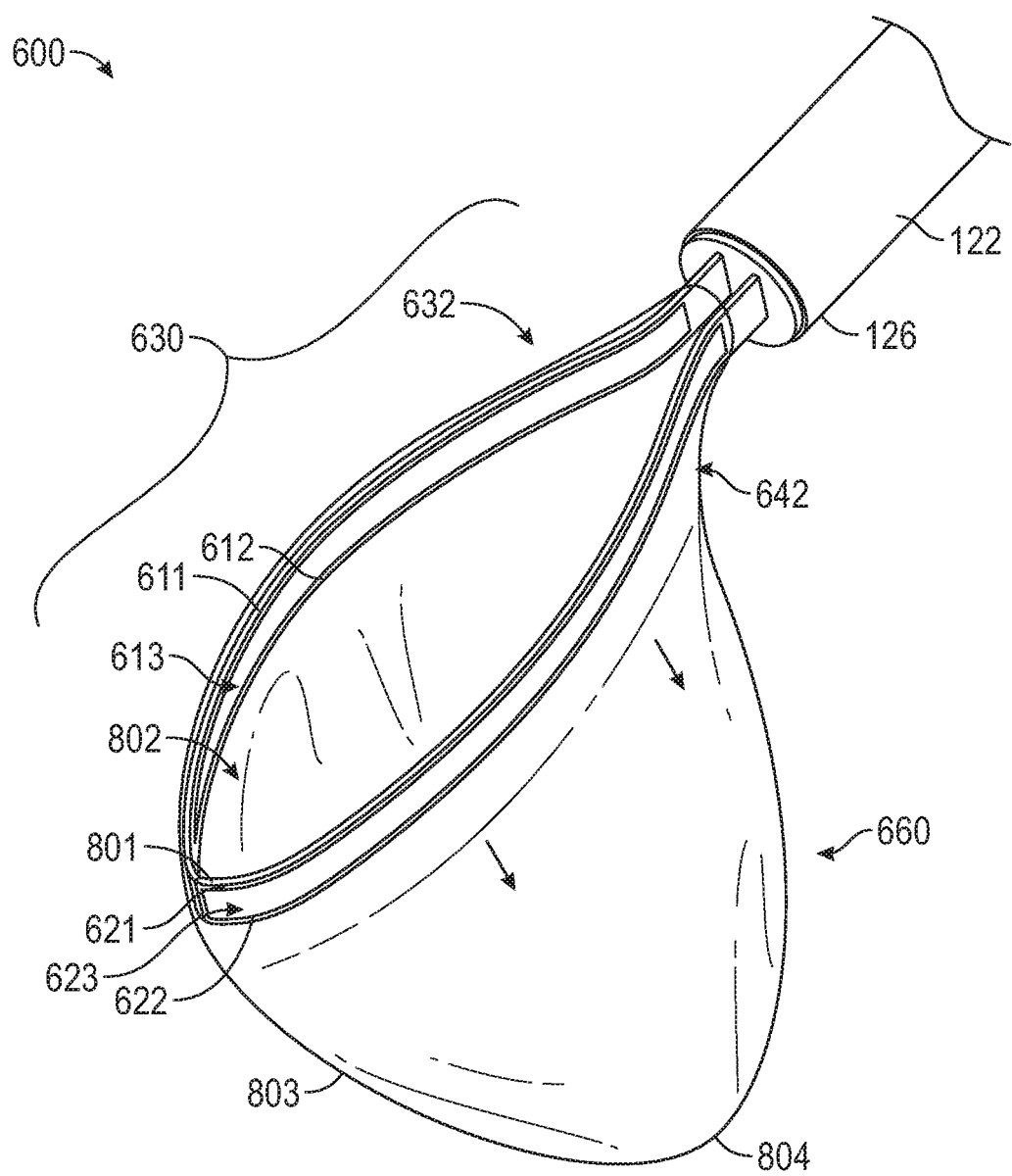
FIG. 6 is a perspective view of a tissue specimen retrieval device including a first arm including a first channel and a second arm including a second channel in an expanded position in accordance with aspects of the present disclosure.
Figure 7A:
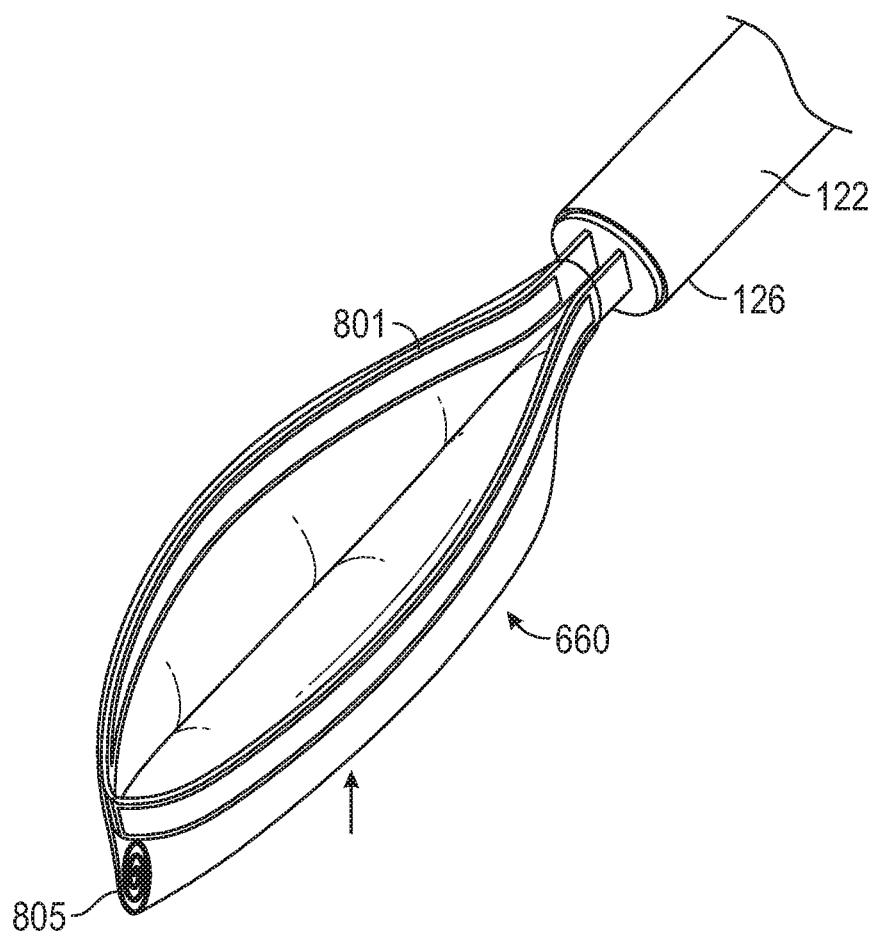
FIG. 7A is a perspective view of a tissue specimen bag of FIG. 6 in a furled state.
Figure 7B:
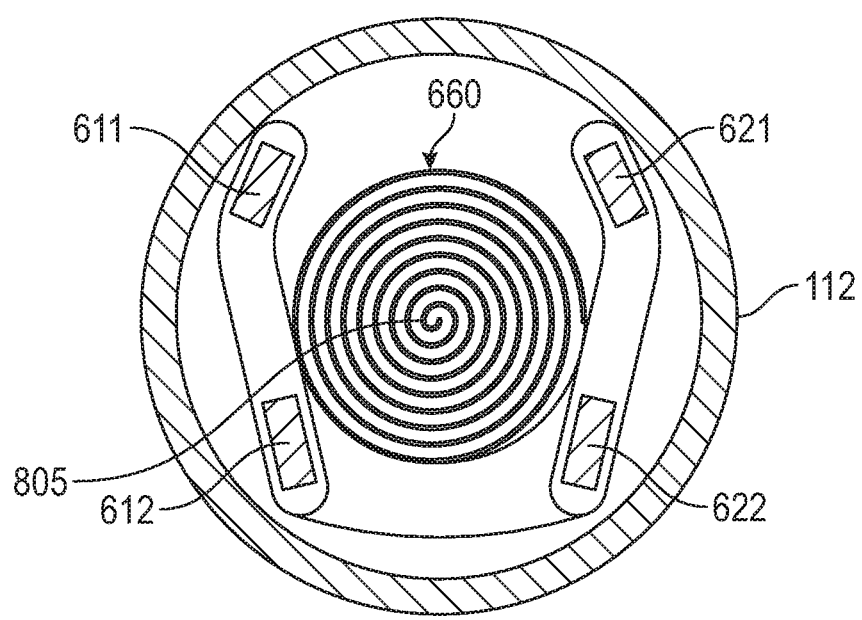
FIG. 7B is a cross-sectional view of the tissue specimen bag of FIG. 6 in the furled state and supported in the first channel and the second channel.
Figure 8:
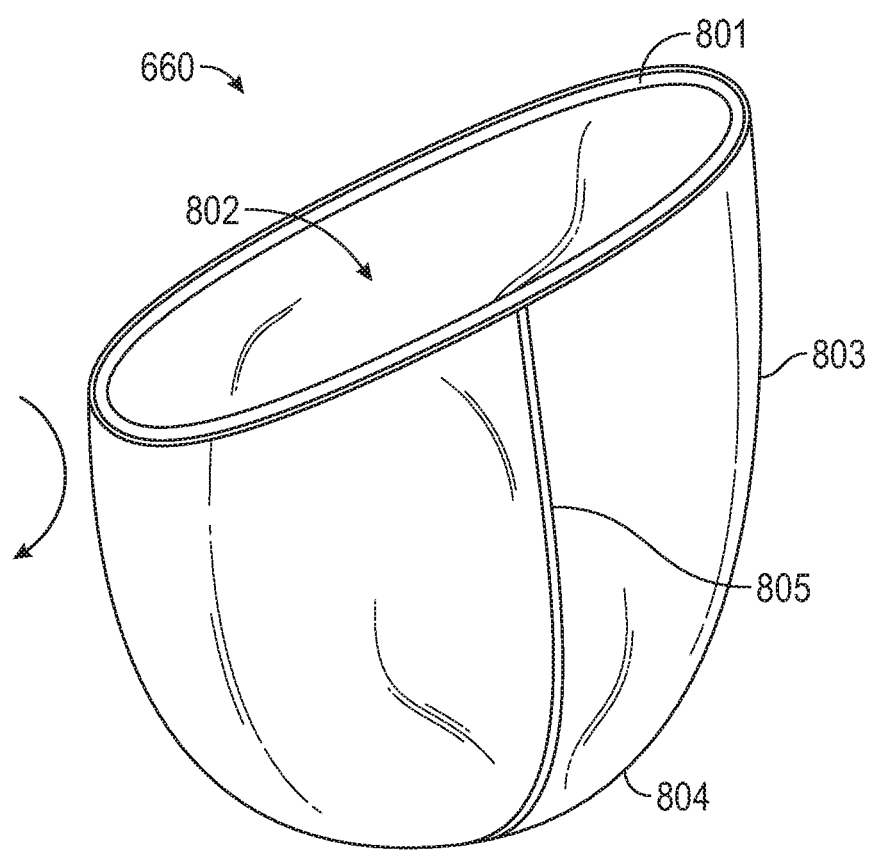
FIG. 8 is a perspective view of the tissue specimen bag of FIG. 6 in an unfurled state.

The second collapse, illustrated in FIGS. 5A and 5B, is a compound collapse corresponding to the flexion and movement about joints 152, 152 of distal segments 136, 146 of arms 132, 142, respectively, from the second expanded position to the second collapsed position, as detailed above, as well as flexion of proximal segments 134, 144 of arms 132, 142 from the first expanded position to the first collapsed position, as also detailed above. These movements corresponding to the second collapse occur within the planes defined by proximal segments 134, 144 and distal segments 136, 146, respectively such that the planes defined by proximal segments 134, 144 and distal segments 136, 146 remain substantially stationary relative to one another during the second collapse.

With additional reference to FIGS. 1 and 2, once the first and second collapses are effected, as detailed above, specimen bag 160 may be folded, twisted, wrapped, rolled, and/or otherwise manipulated relative to arms 132, 142 and, thereafter, second shaft 122 may be pulled proximally relative to first shaft 112, e.g., via moving second handle 128 away from first handle 118, thereby drawing end effector 130 into first shaft 112 to the retracted position. As an alternative to initially manipulating specimen bag 160 relative to arms 132, 142 before drawing end effector 130 into first shaft 112, arms 132, 142 of end effector assembly 130 may instead be at least partially drawn into first shaft 112 followed by manipulating specimen bag 160 to fit within first shaft 112. In other embodiments, rather than effecting the first and second collapses in the deployed position and the retracting end effector assembly 130 proximally into first shaft 112, end effector assembly 130, after the first and second collapses are effected, may be inserted through the proximal end portion 114 of first shaft 112 and moved therethrough to the retracted position, e.g., via manipulating second handle 128. Other suitable configurations for loading end effector assembly 130 within first shaft 112 are also contemplated. Regardless of the loading configuration, once loaded within first shaft 112 in the retracted position, the first and second collapses of arms 132, 142 of end effector assembly 130 are maintained against the biases thereof via the internal spatial constraints of first shaft 112.

Continuing with reference to FIGS. 1 and 2, with end effector assembly 130 loaded within first shaft 112 and tissue specimen retrieval device 100 disposed in the retracted position (FIG. 1), tissue specimen retrieval device 100 is ready for use. More specifically, tissue specimen retrieval device 100 may be inserted into an internal surgical site, e.g., through a suitable access device (not shown), and thereafter moved from the retracted position to the deployed position, e.g., via grasping second handle 128 and moving second handle 128 towards first handle 118.

As end effector assembly 130 is deployed from first shaft 112 and, thus, is no longer constrained by first shaft 112, proximal segments 134, 144 of arms 132, 142 are returned from the first collapsed position to the first expanded position, distal segments 136, 146 of arms 132, 142 are returned from the second collapsed position back to the second expanded position, and distal segments 136, 146 are returned relative to proximal segments 134, 144 from the third collapsed position to the third expanded position. The return to the first, second, and third expanded positions may occur in any order and/or portions thereof may occur substantially simultaneously. Further, upon return to the first, second, and/or third expanded positions, specimen bag 160 is unfurled and open end 162 thereof presented to facilitate insertion of a tissue specimen therein during use.

Unless specified to the contrary below, the tissue specimen retrieval device 600 described in more detail below with reference to FIGS. 6, 7A, 7B and 8 is substantially the same as the tissue specimen retrieval device 100 described above. Thus, wherever technically feasible, the features described with respect to the tissue specimen retrieval device 100 are similarly available to the tissue specimen retrieval device 600 described in more detail below with reference to FIGS. 6-8.

Referring to FIGS. 6, 7A, 7B and 8, a tissue specimen retrieval device 600 includes a first shaft 112 and a second shaft 122 telescopically movable relative to the first shaft 112. The second shaft 122 supports an end effector assembly 630 at a distal end portion 126 thereof. The second shaft 122 is movable relative to the first shaft 112 between a retracted position in which the end effector assembly 630 is disposed within the first shaft 112 (see, e.g., FIGS. 1 and 7B), and a deployed position in which the end effector assembly 630 extends distally from the first shaft 112 (see, e.g., FIGS. 2 and 6).

The end effector assembly 630 includes a tissue specimen bag 660 supported by a first arm 632 and a second arm 642. The first and second arms 632 and 642 extend from the distal end portion 126 of the second shaft 122. A brim 801 defines a bag mouth 802. The bag mouth 802 is an opening in an upper portion of the tissue specimen bag 660 through which a tissue specimen passes to be placed in the tissue specimen bag 660. The first and second arms 632 and 642 open the bag mouth 802 when the second shaft 122 is in the deployed position. A bag body 803 extends from the brim 801 and defines a pouch 804 for a tissue specimen. The pouch 804 may be positioned at a lower portion of the tissue specimen bag 660 to hold the tissue specimen. The bag body 803 reversibly furls and unfurls about the brim 801.

The first arm 632 includes a first upper arm 611 and a first lower arm 612 defining a first channel 613 therebetween. The second arm 642 includes a second upper arm 621 and a second lower arm 622 defining a second channel 623 therebetween. At least a portion of the bag body 803 is supported in the first channel 613 and the second channel 623 when the bag body 803 is furled. The first channel 613 may be unconnected with and spaced apart from the second channel 623.

In some aspects, the first arm 632 or the second arm 642 may be bowed slightly outwardly and/or bowed slightly upwardly to provide additional space for the furled tissue specimen bag 660 as explained in more detail below. This provides increased tension between the first arm 632/the second arm 642 and the tissue specimen bag 660, which assists in loading the tissue specimen bag 660 and prevents the tissue specimen bag 660 from moving with respect to the first arm 632 or the second arm 642. Thus, loading times are reduced and the tissue specimen bag 660 slides relatively easily through the first shaft 112.

In some aspects, the bag body 803 includes one or more spines 805 operably associated with the brim 801 and depending therefrom. The spine 805 reversibly furls and unfurls the bag body 803 about the brim 801. The spine 805 is wound up and positioned between the first and second channels 613 and 623 when the tissue specimen bag 660 is in the first shaft 112, and the spine 805 unwinds when the tissue specimen bag 660 is deployed from the first shaft 112.

In some aspects, the brim 801 includes a shape memory alloy including nickel and/or titanium. In some aspects, the spine 805 includes a shape memory alloy including nickel and/or titanium. A shape-memory alloy is an alloy that can be deformed via temperature or when pressure or tension is applied (e.g., when the brim 801 and the spine 805 are positioned in the first shaft 112), but returns to its original shape when the pressure or tension is removed (e.g., when the brim 801 and the spine 805 are deployed from the first shaft 112). A plurality of spines 805 may be operably associated with the brim to reversibly furl and unfurl the bag body 803.

The first upper arm 611, the first lower arm 612, the second upper arm 621 and/or the second lower arm 622 may each include a shape memory alloy including nickel and/or titanium.

The first arm 632 may be selectively detachable from the second arm 642. In embodiments, the brim 801 has a width of less than about 15 mm.

A method of deploying a tissue specimen bag is also disclosed and includes telescopically advancing a second shaft 122 relative to a first shaft 112. The second shaft 122 supports a tissue specimen bag 660 at a distal end portion 126 thereof. The tissue specimen bag 660 includes a first arm 632 and a second arm 642. The first and second arms 632 and 642 extend from the distal end portion 126 of the second shaft 122. A brim 801 defines a bag mouth 802. A bag body 803 extends from the brim 801 and defines a pouch 804 for a tissue specimen. The bag body 803 includes one or more spines 805 operably associated with the brim 801 and depending therefrom. The spine 805 reversibly furls and unfurls the bag body 803 about the brim 801. The first arm 632 includes a first upper arm 611 and a first lower arm 612 defining a first channel 613 therebetween. The second arm 642 includes a second upper arm 621 and a second lower arm 622 defining a second channel 623 therebetween. The bag body 803 or a portion thereof is supported in the first channel 613 and the second channel 623 when the bag body 803 is furled. The method includes opening the bag mouth 802 by expanding the first and second arms 632 and 642. The bag body 803 is unfurled from the first channel 613 and the second channel 623 by unwinding the spine 805 to expand the pouch 804.

Unless specified to the contrary below, and wherever technically feasible, the tissue specimen retrieval device 900 described in more detail below with reference to FIGS. 9A, 9B and 10 may include any of the features of and/oy may operate in a similar manner as the tissue specimen retrieval devices 100 and/or 600 described above. For example, the methods of deploying a tissue specimen bag described above may similarly be applied to the tissue specimen bag 960 described in more detail below. Thus, these features are not repeated hereinbelow.

Figure 9A:
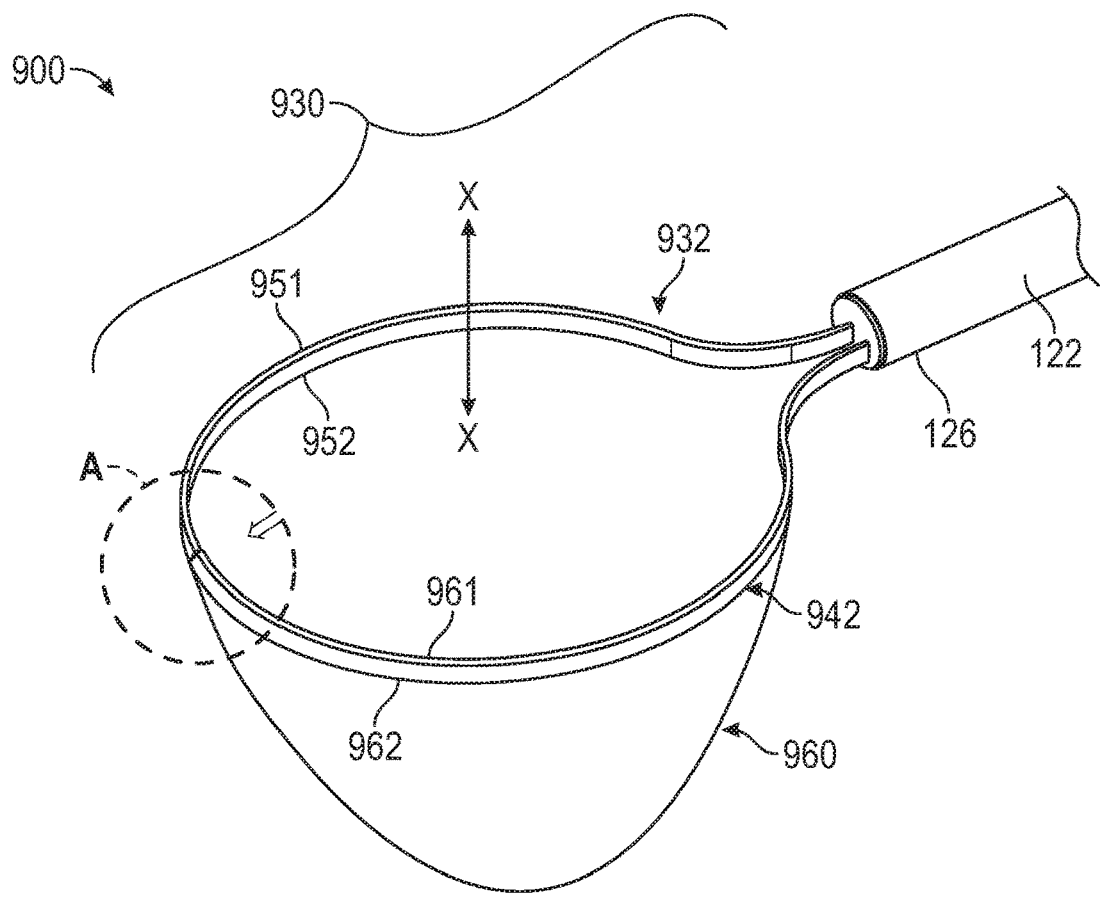
FIG. 9A is a perspective view of a tissue specimen retrieval device including a first arm having a concave inner surface and a second arm having a concave inner surface in an expanded position in accordance with aspects of the present disclosure.
Figure 9B:
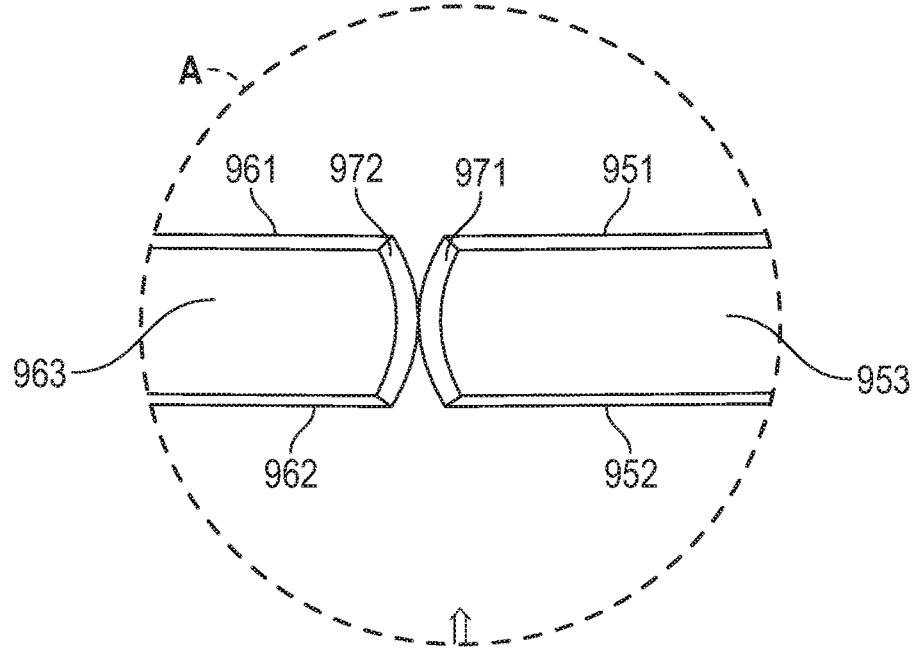
FIG. 9B is an enlarged, inner side view of area A of FIG. 9A.
Figure 10:
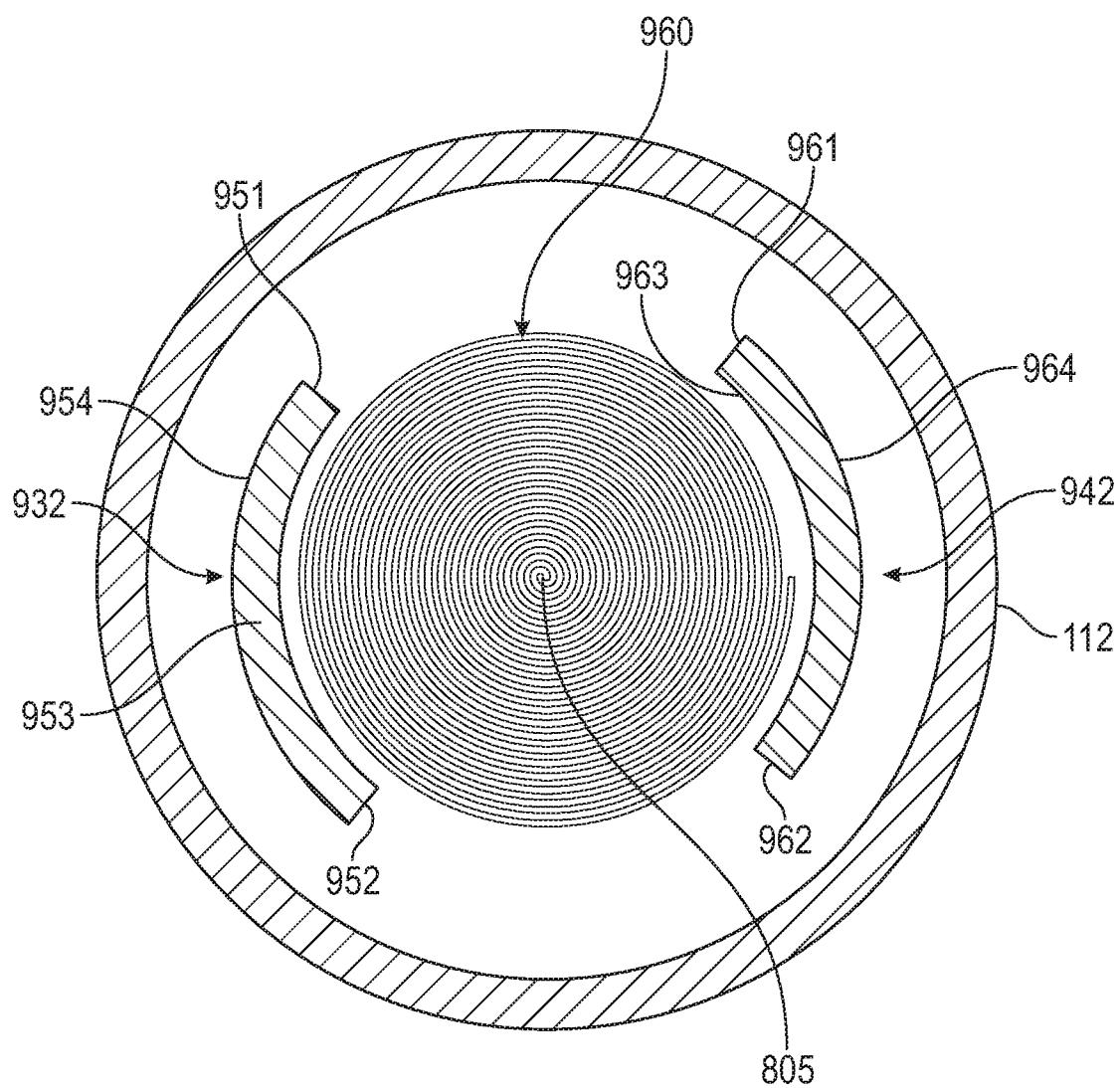
FIG. 10 is a cross-sectional view of the tissue specimen bag of FIG. 9A in the furled state and supported by the first and second arms.

Referring to FIGS. 9A, 9B and 10, the second shaft 122 supports an end effector assembly 930 at a distal end portion 126 thereof. The second shaft 122 is movable relative to the first shaft 112, as described above. The end effector assembly 930 includes a tissue specimen bag 960 supported by a first arm 932 and a second arm 942. The tissue specimen bag 960 is substantially the same as the tissue specimen bag 660 (see, e.g., FIGS. 6, 7A, 7B and 8) described above.

The first arm 932 includes an upper edge 951, a lower edge 952, and a curved inner surface 953 therebetween. The curved inner surface 953 forms a concave shape and supports the tissue specimen bag 960 in a furled state therein (see, e.g., FIG. 10). The second arm 942 includes an upper edge 961, a lower edge 962 and a curved inner surface 963 therebetween. The curved inner surface 963 forms a concave shape and supports the tissue specimen bag 960 in a furled state therein (see, e.g., FIG. 10). As an example, the first arm 932 or the second arm 942 may define a C-shape (e.g., when viewed in a cross-section).

In some aspects, an outer surface 954 of the first arm 932 and/or an outer surface 964 of the second arm 942 may have a convex shape respectively corresponding with the concave shapes of the inner surfaces 953 or 963. Alternatively, the outer surface 954 of the first arm 932 or the outer surface 964 of the second arm 942 may have a substantially round or a substantially flat shape that does not correspond with the concave shapes of the inner surfaces 953 or 963. With momentary particular reference to FIG. 10, in aspects, the configuration of arms 932, 942 and, more specifically, the convex outer surfaces 954, 964 of arms 932, 942, respectively, may be at least partially complementary to the inner surface of first shaft 112 to facilitate fitting end effector assembly 930 therein with tissue specimen bag 960 furled about arms 932, 942.

The first arm 932 may be detachably coupled to the second arm 942 (e.g., at distal ends thereof). Alternatively, the first arm 932 may abut the second arm 942 (e.g., at distal ends thereof) without being attached thereto. Accordingly, the first and second arms 932 and 942 may be selectively released from the tissue specimen bag 960 by being decoupled (if necessary) and retracted from the brim thereof.

In some aspects, the first and second curved inner surfaces 953 and 963 may form a continuous channel having a continuously concave shape supporting the tissue specimen bag 960 in a furled state therein. Alternatively, a first concave channel formed by the curved inner surface 953 of the first arm 932 may be spaced apart from (i.e., may be unconnected with) a second concave channel formed by the curved inner surface 963 of the second arm 942.

The first arm 932 or the second arm 942 may include a shape memory alloy, as described herein. In some aspects, the first arm 932 or the second arm 942 may provide tension between the tissue specimen bag 960 and the first or second inner surfaces 953 and 963 (e.g., when the tissue specimen bag 960 is loaded between the first and second arms 932 and 942 and the first and second arms 932 and 942 are positioned in the first shaft 112).

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
   a first shaft;
   a second shaft telescopically movable relative to the first shaft, the second shaft supporting an end effector assembly at a distal end portion thereof and movable relative to the first shaft between a retracted position, wherein the end effector assembly is disposed within the first shaft, and a deployed position, wherein the end effector assembly extends distally from the first shaft, the end effector assembly including:
   a tissue specimen bag supported by a first arm and a second arm, the first and second arms extending from the distal end portion of the second shaft;
   a brim defining a bag mouth, the first and second arms configured to open the bag mouth when the second shaft is in the deployed position; and
   a bag body extending from the brim and defining a pouch configured to contain a tissue specimen therein, the bag body configured to reversibly furl and unfurl about the brim,
   the first arm including a first upper arm and a first lower arm vertically aligned with the first upper arm, the first arm defining a first channel between the first upper arm and the first lower arm,
   the second arm including a second upper arm and a second lower arm vertically aligned with the second upper arm, the second arm defining a second channel between the second upper arm and the second lower arm,
   wherein at least a portion of the bag body is supported in the first channel and the second channel when the bag body is furled.

2. The tissue specimen retrieval device of claim 1, wherein the bag body includes at least one spine operably associated with the brim and depending therefrom, the at least one spine configured to reversibly furl and unfurl the bag body about the brim.

3. The tissue specimen retrieval device of claim 1, wherein the brim includes a shape memory alloy including at least one of nickel or titanium.

4. The tissue specimen retrieval device of claim 2, wherein the at least one spine includes a shape memory alloy including at least one of nickel or titanium.

5. The tissue specimen retrieval device of claim 1, wherein the brim has a width of less than 15 mm.

6. The tissue specimen retrieval device of claim 1, wherein the furled bag body is supported between the first upper arm, the first lower arm, the second upper arm and the second lower arm in the first shaft when the second shaft is in the retracted position.

7. The tissue specimen retrieval device of claim 1, wherein the first upper arm, the first lower arm, the second upper arm and the second lower arm each include a shape memory alloy including at least one of nickel or titanium.

8. The tissue specimen retrieval device of claim 1, wherein the first arm is selectively detachable from the second arm.

9. A tissue specimen bag, comprising:
   a first arm and a second arm;
   a brim defining a bag mouth, the first and second arms configured to open the bag mouth; and
   a bag body extending from the brim and defining a pouch configured to contain a tissue specimen therein, the bag body configured to reversibly furl and unfurl about the brim,
   the first arm including a first upper arm and a first lower arm vertically aligned with the first upper arm, the first arm defining a first channel between the first upper arm and the first lower arm,
   the second arm including a second upper arm and a second lower arm vertically aligned with the second upper arm, the second arm defining a second channel between the second upper arm and the second lower arm,
   wherein at least a portion of the bag body is supported in the first channel and the second channel when the bag body is furled.

10. The tissue specimen bag of claim 9, wherein the bag body includes at least one spine operably associated with the brim and depending therefrom, the at least one spine configured to reversibly furl and unfurl the bag body about the brim.

11. The tissue specimen bag of claim 10, wherein the at least one spine includes a shape memory alloy including at least one of nickel or titanium.

12. The tissue specimen bag of claim 9, wherein the brim includes a shape memory alloy including at least one of nickel or titanium.

13. The tissue specimen bag of claim 9, wherein the brim has a width of less than 15 mm.

14. The tissue specimen bag of claim 9, wherein the first upper arm, the first lower arm, the second upper arm and the second lower arm each include a shape memory alloy including at least one of nickel or titanium.

15. The tissue specimen bag of claim 9, wherein the first arm is selectively detachable from the second arm.

16. A method of deploying a tissue specimen bag, comprising:

telescopically advancing a second shaft from a first shaft, the second shaft supporting a tissue specimen bag at a distal end portion thereof, the tissue specimen bag including:

a first arm and a second arm, the first and second arms extending from the distal end portion of the second shaft;

a brim defining a bag mouth, the first and second arms configured to open the bag mouth; and a bag body extending from the brim and defining a pouch configured to contain a tissue specimen therein, the bag body including at least one spine operably associated with the brim and depending therefrom, the at least one spine configured to reversibly furl and unfurl the bag body about the brim, the first arm including a first upper arm and a first lower arm vertically aligned with the first upper arm, the first arm defining a first channel between the first upper arm and the first lower arm, the second arm including a second upper arm and a second lower arm vertically aligned with the second upper arm, the second arm defining a second channel between the second upper arm and the second lower arm, wherein at least a portion of the bag body is supported in the first channel and the second channel when the bag body is furled;

opening the bag mouth by expanding the first and second arms to expand the brim; and unfurling the bag body from the first channel and the second channel by unwinding the at least one spine to expand the pouch.

17. The method of claim 16, wherein the brim includes a shape memory alloy including at least one of nickel or titanium.

* * * * *